(12) United States Patent
Chieng

(10) Patent No.: US 7,458,990 B2
(45) Date of Patent: Dec. 2, 2008

(54) DEVICE FOR PROTECTING FEMORAL NECK

(76) Inventor: Poon-Ung Chieng, 1F 155 Sung-ren Road, Taipei (TW)

( * ) Notice: Subject to any disclaimer, the term of this patent is extended or adjusted under 35 U.S.C. 154(b) by 152 days.

(21) Appl. No.: 10/489,603

(22) PCT Filed: Aug. 19, 2002

(86) PCT No.: PCT/CN02/00571

§ 371 (c)(1),
(2), (4) Date: Mar. 19, 2004

(87) PCT Pub. No.: WO03/024345

PCT Pub. Date: Mar. 27, 2003

(65) Prior Publication Data

US 2004/0260399 A1 Dec. 23, 2004

(30) Foreign Application Priority Data

Sep. 21, 2001 (CN) .......................... 01 2 63640

(51) Int. Cl.
*A61F 2/36* (2006.01)
(52) U.S. Cl. .................................................. 623/23.12
(58) Field of Classification Search ............. 623/20.35, 623/20.36, 23.11, 23.12, 23.13, 23.14, 23.15, 623/23.21, 23.22, 23.26, 23.27, 23.35
See application file for complete search history.

(56) References Cited

U.S. PATENT DOCUMENTS

| | | | | |
|---|---|---|---|---|
| 2,668,531 A * | 2/1954 | Haboush | .................. | 623/23.13 |
| 3,053,251 A * | 9/1962 | Black et al. | .............. | 623/23.12 |
| 3,818,512 A * | 6/1974 | Shersher | .................. | 623/22.15 |
| 3,818,514 A * | 6/1974 | Clark | ....................... | 623/22.12 |
| 4,224,699 A * | 9/1980 | Weber | ...................... | 623/23.14 |
| 4,532,660 A * | 8/1985 | Field | ....................... | 623/23.42 |
| 4,846,841 A * | 7/1989 | Oh | .......................... | 623/23.13 |
| 4,911,720 A * | 3/1990 | Collier | .................... | 623/23.12 |
| 5,087,260 A | 2/1992 | Fixel | | |
| 5,133,769 A * | 7/1992 | Wagner et al. | ........... | 623/23.13 |
| 5,275,603 A * | 1/1994 | Ferrante et al. | ............... | 606/86 |
| 5,858,020 A * | 1/1999 | Johnson et al. | .......... | 623/23.15 |
| 6,383,227 B1* | 5/2002 | Baroud et al. | ............ | 623/23.22 |
| 6,488,716 B1* | 12/2002 | Huang et al. | ............. | 623/23.12 |
| 6,706,073 B2* | 3/2004 | Draenert et al. | .......... | 623/22.46 |

FOREIGN PATENT DOCUMENTS

| | | |
|---|---|---|
| CN | 2318995 Y | 5/1999 |
| EP | 0 393 608 A2 | 10/1990 |
| GB | 2090745 A | 7/1982 |

\* cited by examiner

*Primary Examiner*—Eduardo C Robert
*Assistant Examiner*—David Comstock
(74) *Attorney, Agent, or Firm*—Bacon & Thomas, PLLC

(57) ABSTRACT

A femoral neck protection device comprises a main body disposed with a hollow sleeve, and a flange extended outwardly from a peripheral rim at one end of the sleeve. At least one aperture is disposed on the flange. A protruding neck portion is disposed at the other end of the sleeve. A bolt disposed inside the neck portion passing through the sleeve and being secured to a prepared femur is engaged with an artificial ball head of the femur.

6 Claims, 5 Drawing Sheets

DEVICE FOR PROTECTING FEMORAL NECK

BACKGROUND OF THE INVENTION

A. Field of the Invention

The present invention relates to a femoral neck protection device.

B. Description of the Prior Art

In general, the surgical operation for installing an artificial hip joint currently adopted by hospitals usually saws femoral neck first, and then inserts a metal femoral stem into a intramedullary cavity and fills the intramedullary cavity with bone cement for the fixation. However, such structure usually creates a change of stress distribution to the femur and results in an unstable fixation. Further, the newly grown blood vessel and callous formation cannot efficiently cover the metal of the metal femur rod. As a result, the metal femur rod fails to integrally connect with the femur for protecting the femur, and thus may loosen the fractured femur and the covered metal due to the limited sustaining strength. Such arrangement usually makes a patient suffer painfully and go through an unnecessary surgical operation again for repairs, adjustments, or corrections. The aforementioned shortcomings have bothered medical professionals and patients for a long time.

To improve the above mentioned shortcomings, the R.O.C. Utility Model Patent with Publication No. 2318995 published on May 19, 1999 disclosed an stemless hip prosthesis, which comprises a modular head; a device for protecting femoral neck and a central femoral screw; wherein said modular neck is in a major hemispherical shape, and a concave frustum hole is disposed at an end of the cross section of the external surface of the sphere, and said device for protecting femoral neck is a hollow, and cylindrical femoral neck which has an anatomical collar. There is a hole at the top of the anatomical collar for receiving the insertion of the corresponding central femoral screw. And the said central femoral screw is a threaded rod being inserted into the hole at the top of the device for protecting femoral neck. The nail cap and the device for protecting femoral neck are at the same level and tightly bounded. In the procedure of clinical tests, many unreasonable points are found, such as that the device for protecting femoral neck is a hollow bell-shape and its shape is irregular, therefore it is unable to produce an accessory tool for performing a specific surgical operation for the irregular femoral neck. As a result, a patient may need another surgical operation due to the failure of the previous one.

SUMMARY OF THE INVENTION

The primary objective of the present invention is to provide a protective device in a regular geometric shape that can be connected directly to a trimmed femoral neck, so as to overcome the foregoing existing shortcomings.

This invention comprises a main body having a sleeve with a hollow interior. The sleeve is in a regular geometric shape after being trimmed and connected to the femoral neck in a regular geometric shape; a flange extended outwardly from a peripheral rim at one end of the sleeve; a protruding neck portion disposed at the other end of the sleeve and facing inwardly; a bolt disposed on the neck portion that passes through the neck of the femur inside the sleeve; at least one aperture disposed on the main body for receiving a fastener fixed onto the femoral neck; and a modular head of a device for protecting femoral neck coupled to the sleeve at an end away from the neck portion for freely moving the hip joint.

Since this invention adopts a regular geometric sleeve, therefore the flange can be attached tightly onto the surface of the femur.

DETAILED DESCRIPTION OF THE PREFERRED EMBODIMENTS

Figure 1:
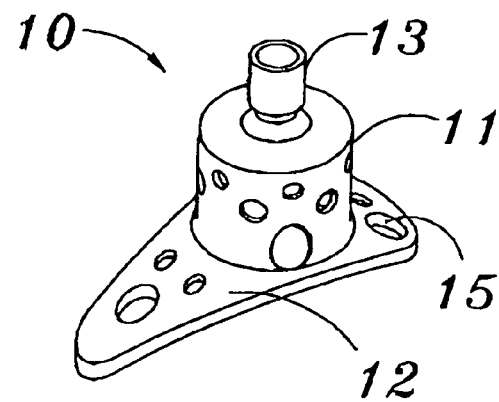
FIG. 1 is a perspective view of the present invention of the device for protecting femoral neck.
Figure 2:
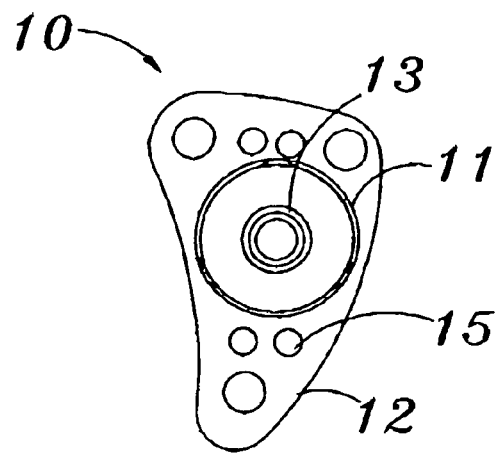
FIG. 2 is a top view of the present invention of the device for protecting femoral neck.
Figure 3:
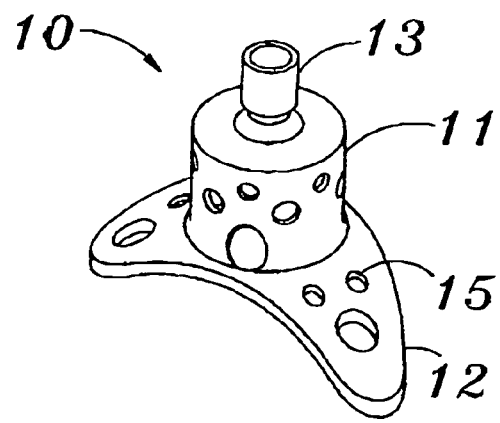
FIG. 3 is another perspective view of the present invention of the device for protecting femoral neck.
Figure 4:
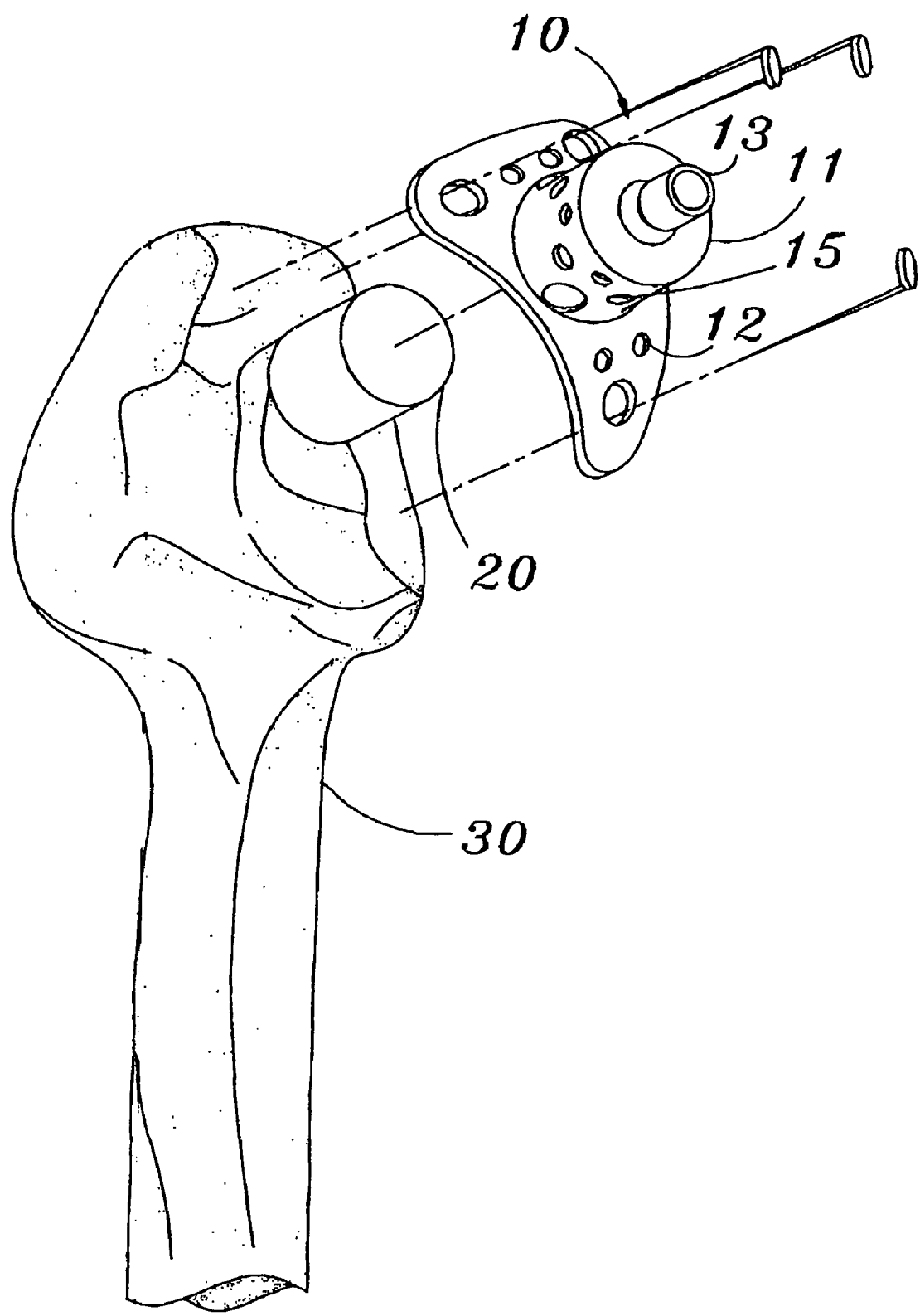
FIG. 4 is an exploded view of the present invention of the device for protecting femoral neck.
Figure 6:
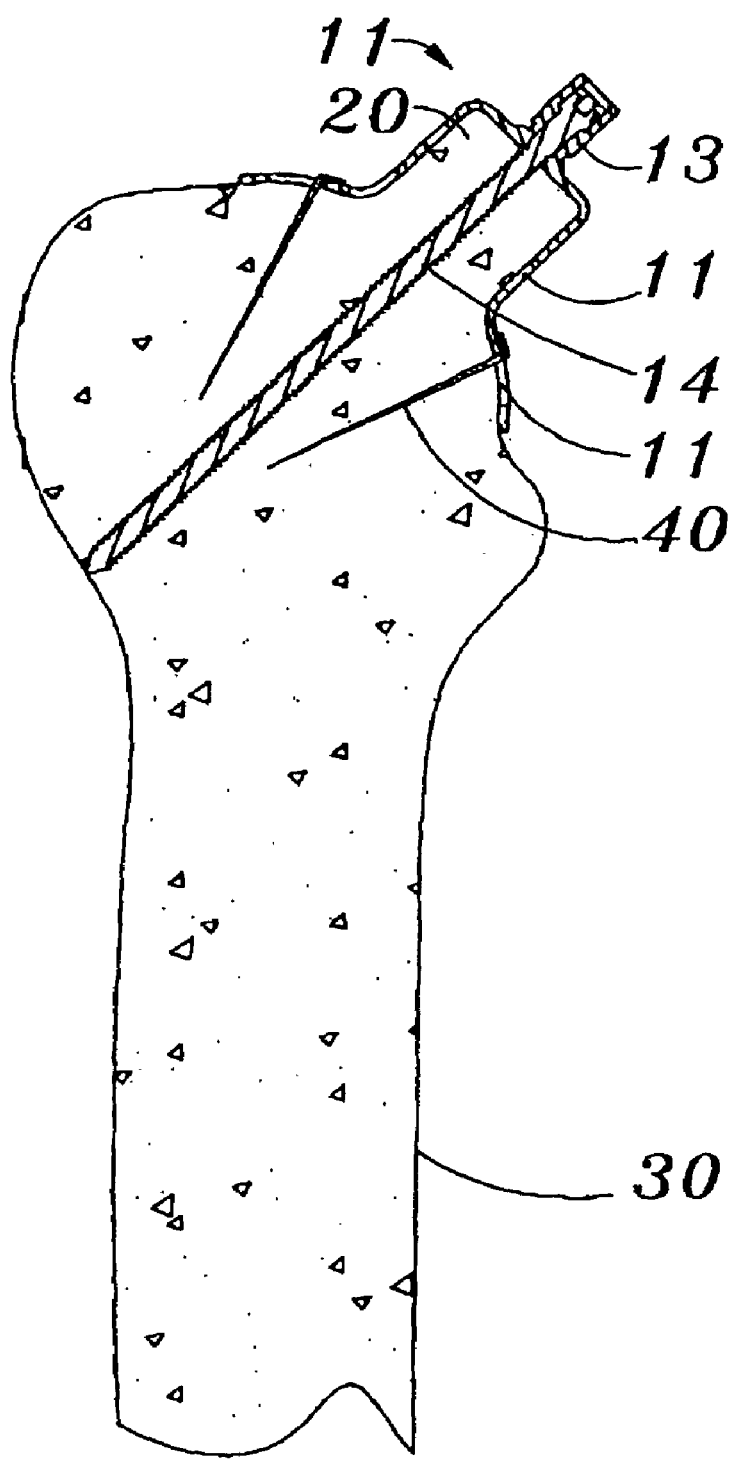
FIG. 6 is a cross-sectional view of the present invention of the device for protecting femoral neck.
Figure 7:
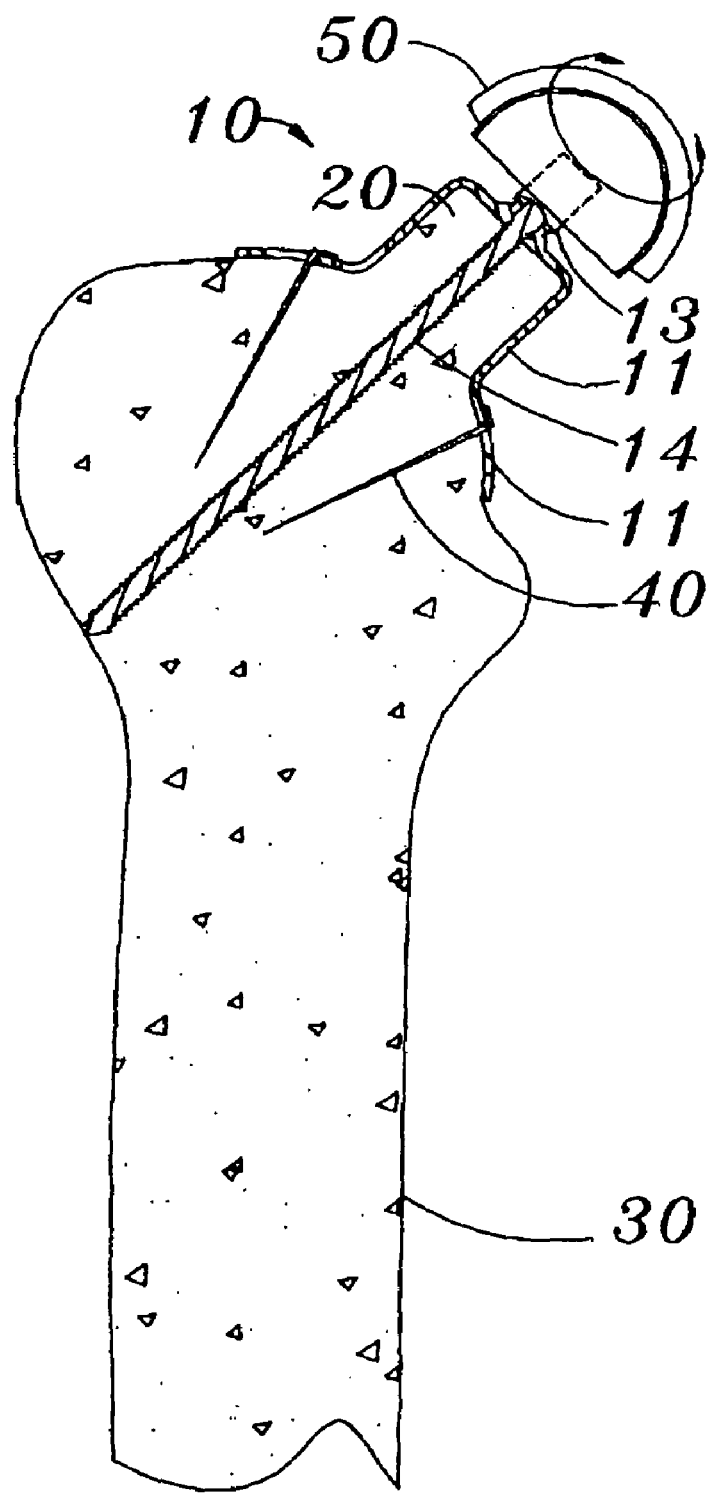
FIG. 7 is a schematic view of the connection between the femoral neck and the present invention of the device for protecting femoral neck.

Referring to FIGS. 1, 2, and 3, present invention of the device for protecting femoral neck is capable of steadily securing and covering in a geometric shape after being trimmed as well as integrally connected with the new-grown blood vessels and callous formation. A main body (10) with a hollow sleeve (11) is disposed on the device; a flange (12) in a geometric shape which is slightly arcuate (a triangular flange (12) is adopted in this embodiment) is extended outwardly from a peripheral rim of an end of the sleeve (11). A neck portion (13) is extended from the other end of the sleeve (11) and a bolt (14) as shown in FIG. 6 is inserted into the neck portion (13). A threaded head is disposed at an end of the bolt 14 and a thread is disposed at the other end of the bolt 14. Furthermore, at least one aperture (15) is disposed on the main body (10) and sleeved with a fastener (40) as shown in FIG. 4. A bone nail is used as the fastener (40) in this embodiment.

Figure 5:
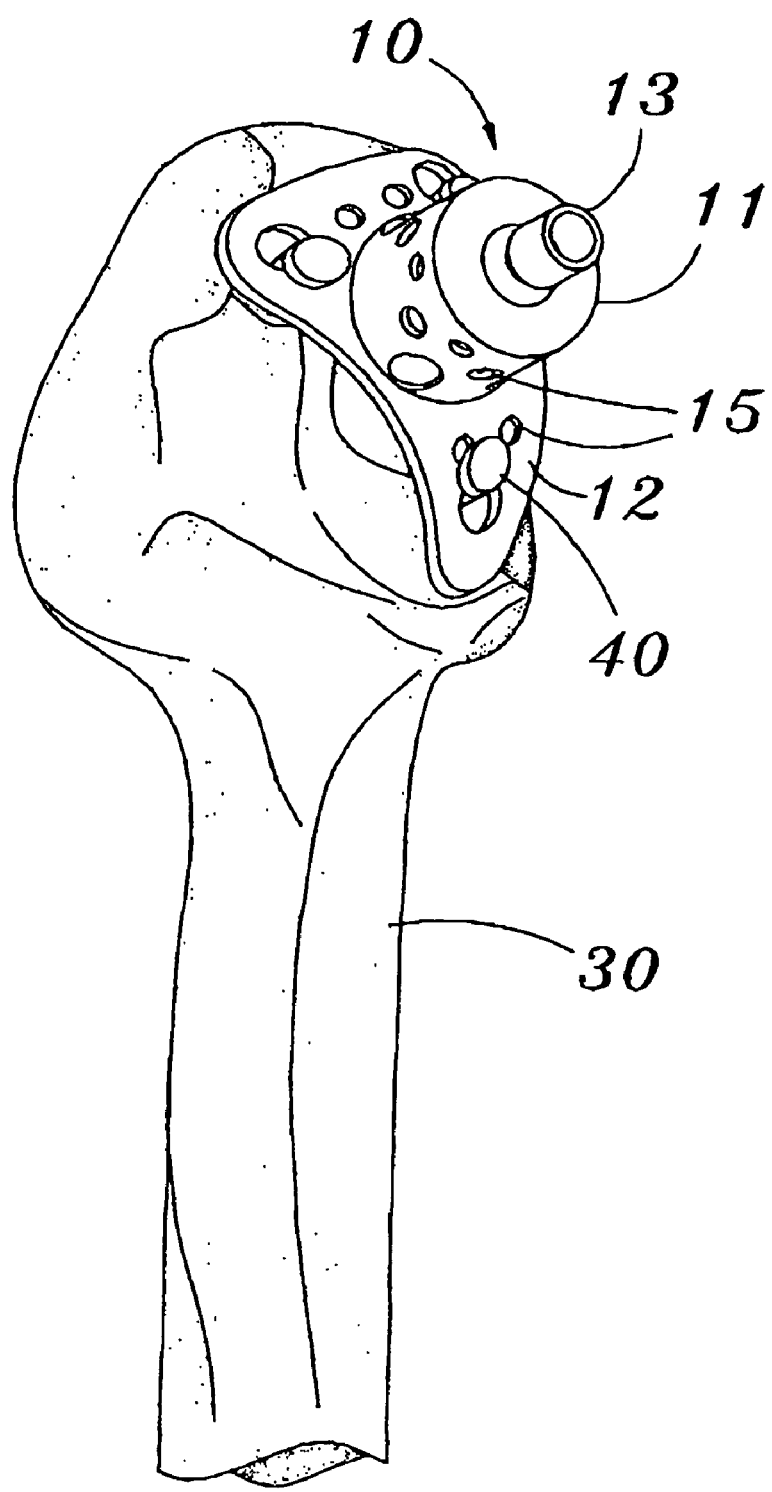
FIG. 5 is a perspective view of the present invention of the device for protecting femoral neck.

When the protective device of the present invention is in use as shown in FIGS. 4, 5, 6 and 7, the femoral neck (20) is trimmed in a surgical operation to fit the geometric shape of the sleeve (11), and then the sleeve (11) of the main body (10) is connected to the femoral neck (20) thereby tightly affixing the flange (12) thereof to the surface where the femur (30) and the neck of the femur (20) are connected; the bolt (14) passes through the trimmed femoral neck (20) and connects with the sleeve (11) to be secured onto the femur (30) as shown in FIGS. 5 and 6. Therefore, not only the main body (10) is securely connected with the trimmed femoral neck, the protection of the main body (10) also allows the femoral neck (20) to grow again. Since the sleeve 11 is in a geometric cylindrical shape and made into a special-purpose surgical operation tool, therefore the present invention makes such surgical operation possible.

Further, the fastener (40) being passed through the aperture (15) and secured onto the femur (30) reinforces the connection between the femur (30) and the femur diaphysis (not shown in the Figures) to prevent rotations and also prevents the flange (12) of the main body (10) from being loosened and separated.

The aperture (15) disposed on the main body (10) is capable of allowing the new-grown blood vessels and callous formation to penetrate there through and cover the main body

(10) as well as connecting with the femoral neck (20) and the femur (30) into one unit. Furthermore, an artificial ball head of the femur (50) is disposed on the neck portion (13) at an end away from the sleeve (11) for connecting with the bolt (14) by its internal thread, such that the ball head (50) of the femur allows the hip joint connected to the femur (30) to move freely.

Of course, the foregoing fastener can be substituted by any component other than the bone nail, and the foregoing sleeve can be substituted by any geometric shape other than the geometric cylindrical shape, flange can be any shape adjustable to the femoral neck, the body of the bolt can come with no threads, and the artificial ball head of the femur can be fixed by bolts. It is understood that the embodiment described herein is merely illustrative of the principles of the invention and that a wide variety of modifications thereto may be effected by persons skilled in the art without departing from the spirit and scope of the invention as set forth in the following claims.

The invention claimed is:

1. A device for protecting a femoral neck, comprising:
a main body, the main body comprising a right geometric cylindrical shaped hollow sleeve configured for housing a femoral neck therein, and having a lower rim and an upper rim and that corresponds to a trimmed femoral neck; a geometric-shaped flange extending outwardly from the periphery of the lower rim of the hollow sleeve; and a neck extending from the upper rim of the hollow sleeve, wherein a bolt is fixed at the top of the neck and is arranged to penetrate a femur neck; and
wherein the main body further comprises at least one hole, the at least one hole adaptable for receiving a fastener configured to be fixed onto a femur.

2. The device for protecting a femoral neck of claim 1, wherein said geometric-shaped flange is adapted to be disposed on a substantially curved surface that connects a femur and a femoral neck.

3. The device for protecting a femoral neck of claim 2, wherein said geometric-shaped flange is adapted to be disposed on a substantially triangular surface that connects a femur and a femoral neck.

4. The device for protecting a femoral neck of claim 1, wherein an end of said bolt comprises a threaded head and a threaded bolt section.

5. The device for protecting a femoral neck of claim 4, wherein said neck at an end away from said right geometric cylindrical shaped hollow sleeve comprises an inner thread for passing said bolt through and wherein an artificial ball head is coupled with the threaded bolt section.

6. The device for protecting a femoral neck of claim 1 wherein said fastener is a bone nail.

* * * * *